United States Patent [19]
Hoffmann et al.

[11] 3,981,994
[45] Sept. 21, 1976

[54] O-ALKYL-O-[1-PHENYL-5-CYANOALKYLMERCAPTO-1,2,4-TRIAZOL(3)YL]-THIONOPHOSPHORIC(-PHOSPHONIC) ACID ESTERS

[75] Inventors: Hellmut Hoffmann, Wuppertal; Ingeborg Hammann, Cologne; Wilhelm Stendel, Wuppertal, all of Germany

[73] Assignee: Bayer Aktiengesellschaft, Leverkusen, Germany

[22] Filed: Jan. 9, 1975

[21] Appl. No.: 539,898

[30] Foreign Application Priority Data
Jan. 26, 1974  Germany............................ 2403711

[52] U.S. Cl................................ 424/200; 260/308 R; 260/308 C
[51] Int. Cl.[2]...................... A01N 9/36; C07F 9/165; C07F 9/40
[58] Field of Search.................. 424/200; 260/308 R

[56] References Cited
UNITED STATES PATENTS

| | | |
|---|---|---|
| 2,754,244 | 7/1956 | Gysin et al............................ 424/200 |
| 3,867,397 | 2/1975 | Bohner et al. .................. 260/308 R |

FOREIGN PATENTS OR APPLICATIONS

| | | |
|---|---|---|
| 2,259,960 | 6/1973 | Germany......................... 260/308 R |

Primary Examiner—Alton D. Rollins
Attorney, Agent, or Firm—Burgess, Dinklage & Sprung

[57] ABSTRACT

O-alkyl-O-[1-phenyl-5-cyanoalkylmercapto-1,2,4-triazol(3)yl]-thionophosphoric (phosphonic) acid esters of the formula

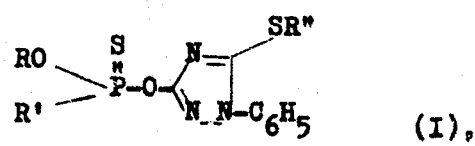

in which
R is alkyl with 1 to 6 carbon atoms,
R' is alkyl or alkoxy with in either case 1 to 6 carbon atoms, and
R'' is cyanoalkyl with 1 to 4 carbon atoms, which possess insecticidal, acaricidal and nematicidal properties.

9 Claims, No Drawings

O-ALKYL-O-[1-PHENYL-5-CYANOALKYLMER-CAPTO-1,2,4-TRIAZOL(3)YL]-THIONOPHOSPHORIC(PHOSPHONIC) ACID ESTERS

The present invention relates to and has for its objects the provision of particular new O,O-dialkyl-O-[1-phenyl-5-cyanoalkylmercapto-1,2,4-triazol(3)yl]-thionophosphoric acid esters and their alkanethionophosphonic acid ester counterparts, which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from U.S. Pat. No. 2,754,244 and German Published Specification DOS 2,259,960 that pyrazolothionophosphoric acid esters, for example O,O-dimethyl-(Compound A) or O,O, diethyl-O-[3-methyl-pyrazol(5)yl]-thionophosphoric acid ester (Compound B), and triazolothionophosphoric acid esters, for example O,O-dimethyl-(Compound C) or O,O-diethyl-O-[1-methyl-5-methylmercapto-1,2,4-triazol(3)yl]- (Compound D) or O,O-dimethyl-O-[1-ethyl-5-methylmercapto-1,2,4-triazol(3)yl]-thionophosphoric acid ester (Compound E), possess insecticidal and acaricidal properties.

The present invention provides, as new compounds, the O-triazolylthionophosphoric(phosphonic) acid esters of the general formula

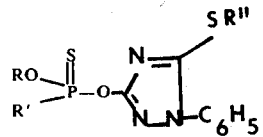

in which
R is alkyl with 1 to 6 carbon atoms,
R' is alkyl or alkoxy with in either case 1 to 6 carbon atoms, and
R" is cyanoalkyl with 1 to 4 carbon atoms.

Preferably, R is straight-chain or branched alkyl with 1 to 5, especially 1 to 4, carbon atoms, R' is straight-chain or branched alkyl or alkoxy with in either case 1 to 5, especially 1 to 4, carbon atoms, and R" is cyanoalkyl with 1 to 3 carbon atoms.

Surprisingly, the O-triazolylthionophosphoric(phosphonic) acid esters according to the invention show a better insecticidal and acaricidal action than the previously known compounds of analogous structure and of the same type of action. They act not only against insects and mites which are harmful to plants, but also against ectoparasites, for example parasitic fly larvae, in the veterinary medicine field. The compounds according to the invention thus represent a genuine enrichment of the art.

The present invention also provides a process for the preparation of an O-triazolylthionophosphoric(phosphonic) acid ester of the formula (I), in which a thionophosphoric-(phosphonic) acid diester halide of the general formula

in which
R and R' have the above-mentioned meanings, and
Hal is halogen, preferably chlorine,
is reacted with a hydroxytriazole derivative of the general formula

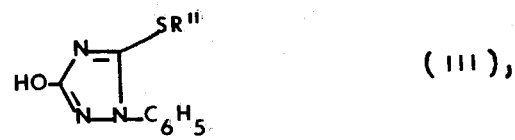

in which
R" has the above-mentioned meaning,
the latter being reacted as such in the presence of an acid-binding agent, or in the form of an alkali metal salt, alkaline earth metal salt or ammonium salt thereof.

If, for example O,O-dimethylthionophosphoric acid diester chloride and 1-phenyl-3-hydroxy-5-cyanomethylmercaptotriazole-(1,2,4) are used as starting materials, the course of the reaction can be represented by the following equation:

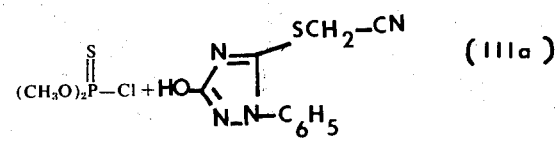

(IIa)

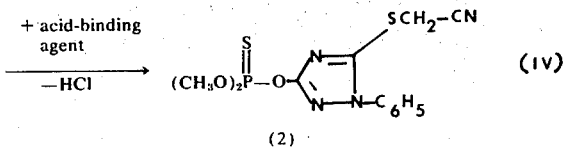

(2)

The thionophosphoric(phosphonic) acid ester halide (II) to be used as starting materials are known from the literature and can be prepared according to generally customary processes, even on a large industrial scale.

The following may be mentioned as examples thereof: O,O-dimethyl-, O,O-diethyl-, O,O-di-n-propyl-, O,O-diisopropyl-, O,O-di-n-butyl-, O,O-di-isobutyl-, O,O-di-tert.-butyl-, O-ethyl-O-n-propyl-, O-ethyl-O-isopropyl- or O-ethyl-O-sec.-butyl-thionophosphoric acid ester chloride and O-methyl-, O-ethyl-, O-n-propyl-, o-isopropyl-, O-n-butyl-, O-sec.-butyl-, O-isobutyl- or O-tert.-butyl-methane-, -ethane-, -n-propane-, -isopropane-, n-butane-, -isobutane-, -sec.-butane-or -tert.-butane-thionophosphonic acid ester chloride.

The triazoles of the formula (III), which in some cases are new, can be prepared according to processes which are known in principle. For example, halogenocarbonic acid alkyl esters are reacted with potassium thiocyanate and subsequently with phenylhydrazine to give the intermediate of the formula

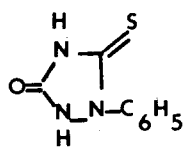

which can then be converted to the desired hydroxytriazoles (III) by reaction with halogenoalkanecarboxylic acid nitriles in the presence of alcoholates.

The following may be mentioned as examples of the triazole derivatives (III) to be used as starting materials:

5-cyanomethylmercapto-, 5-(2-cyanoethylmercapto)-, 5-(1-cyanoethylmercapto)- or 5-(3-cyanopropylmercapto)-3-hydroxy-1-phenyltriazole-(1,2,4).

The preparative process is preferably carried out with conjoint use of suitable solvents and diluents. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-acceptors can be used as acid-binding agents. Alkali metal carbonates and alkali metal alcoholates, such as sodium carbonate, methylate and ethylate, and potassium carbonate, methylate and ethylate, have proved particularly suitable, as have aliphatic, aromatic or heterocyclic amines, for example triethylamaine, trimethylamine, dimethylaniline, dimethylbenzylamine and pyridine.

The reaction temperature can be varied within a fairly wide range. In general, the reaction is carried out at between 0° and 120°C, preferably at from 15° to 80°C.

In general, the starting components are employed in equimolar amounts in carrying out the process. An excess of one or other reactant produces no significant advantages. The reaction is preferably carried out in one of the above-mentioned solvents in the presence of an acid-acceptor at the indicated temperatures, while stirring the mixture, and after a period of reaction of 1 or more hours — in most cases at elevated temperatures — the reaction mixture is worked up in accordance with customary methods. In general, the reaction solution is poured into water and taken up in an organic solvent, for example benzene, the organic phase is washed and dried, and the solvent is distilled off under reduced pressure.

The new compounds are frequently obtained in the form of oils which in most cases cannot be distilled without decomposition but can be freed from the last volatile constituents by so-called "slight distillation", that is to say by prolonged heating under reduced pressure to moderately elevated temperatures, and can be purified in this way. They are characterized by their refractive indexes. Others of the products are obtained in a crystalline form with sharp melting point.

As has already been mentioned, the O-triazolylthionophosphoric(phosphonic) acid esters according to the invention are distinguished by an outstanding insecticidal and acaricidal activity. They act not only against plant pest, pests harmful to health and pests of stored products, but also, in the veterinary medicine field, against animal parasites (ectoparasites), such as parasitic fly larvae. The products possess low phytotoxicity and a good action both against sucking and against biting insects. In addition, some of the compounds show a nematicidal activity.

For this reason, the new compounds can be employed successfully as pesticides in plant protection and in the hygiene field, the field of protection of stored products and the veterinary field.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma guadrate*), the red cotton bug (*Dysdercus intermedius*), the bed bug (*Cimex lectularius*), the assassin bug (*Rhodnius prolixus*) and Chagas' bug (*Triatoma*

*infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera) for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite *Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the novel products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%., preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, and more particularly methods of combating insects and acarids, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae were killed, whereas 0% means that none of the beetle larvae were killed.

The active compounds, the concentrations of the active compounds, the evaluation times and the results can be seen from the following table:

TABLE 1

| (Phaedon larvae test) | | |
|---|---|---|
| Active compound | Active compound concentration in % | Degree of destruction in % after 3 days |
| 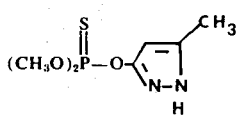 (A) (known) | 0.1 | 0 |
| 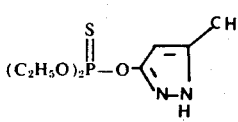 (B) | 0.1<br>0.01<br>0.001 | 100<br>100<br>0 |

TABLE 1-continued (Phaedon larvae test)

| Active compound | Active compound concentration in % | Degree of destruction in % after 3 days |
|---|---|---|
| (known) $(CH_3O)_2\overset{S}{\underset{\|}{P}}-O-\underset{N-N}{\overset{N=}{\bigg\langle}}\underset{CH_3}{\overset{SCH_3}{\bigg\rangle}}$ (C) | 0.1<br>0.01<br>0.001 | 100<br>100<br>0 |
| (known) $(C_2H_5O)_2\overset{S}{\underset{\|}{P}}-O-\underset{N-N}{\overset{N=}{\bigg\langle}}\underset{CH_3}{\overset{SCH_3}{\bigg\rangle}}$ | 0.1<br>0.01<br>0.001 | 100<br>100<br>0 |
| $(CH_3O)_2\overset{S}{\underset{\|}{P}}-O-\underset{N-N}{\overset{N=}{\bigg\langle}}\underset{C_2H_5}{\overset{SCH_3}{\bigg\rangle}}$ (E) | 0.1<br>0.01<br>0.001 | 100<br>100<br>0 |
| (known) $(C_2H_5O)_2\overset{S}{\underset{\|}{P}}-O-\underset{N-N}{\overset{N=}{\bigg\langle}}\underset{C_6H_5}{\overset{SCH_2-CN}{\bigg\rangle}}$ (1) | 0.1<br>0.01<br>0.001 | 100<br>100<br>95 |
| $(CH_3O)_2\overset{S}{\underset{\|}{P}}-O-\underset{N-N}{\overset{N=}{\bigg\langle}}\underset{C_6H_5}{\overset{SCH_2-CN}{\bigg\rangle}}$ (2) | 0.1<br>0.01<br>0.001 | 100<br>100<br>70 |
| $\underset{C_2H_5}{\overset{C_2H_5O}{\diagdown}}\overset{S}{\underset{\|}{P}}-O-\underset{N-N}{\overset{N=}{\bigg\langle}}\underset{C_6H_5}{\overset{SCH_2-CN}{\bigg\rangle}}$ (3) | 0.1<br>0.01<br>0.001 | 100<br>100<br>100 |
| $(C_2H_5O)_2\overset{S}{\underset{\|}{P}}-O-\underset{N-N}{\overset{N=}{\bigg\langle}}\underset{C_6H_5}{\overset{SCH_2-CH_2-CN}{\bigg\rangle}}$ (4) | 0.1<br>0.01<br>0.001 | 100<br>100<br>100 |

EXAMPLE 2

Plutella test

Solvent: 3 parts by weight of acetone
Emulsifier: 1 part by eight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed, whereas 0% means that none of the caterpillars were killed.

The active compounds, the concentrations of the active compounds, the evaluation times and the results can be seen from the following table:

EXAMPLE 3

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed, whereas 0% means that none of the aphids were killed.

The active compounds, the concentrations of the active compounds, the evaluation times and the results can be seen from the following table:

TABLE 2

(Plutella test)

| Active compound | Active compound concentration in % | Degree of destruction in % after 3 days |
|---|---|---|
| 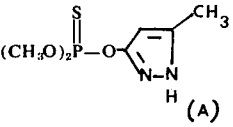 (A) (known) | 0.1 | 0 |
| 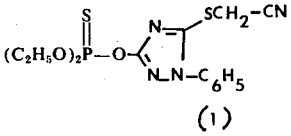 (1) | 0.1<br>0.01<br>0.001 | 100<br>100<br>100 |
| 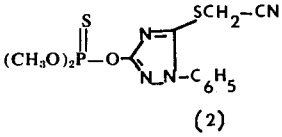 (2) | 0.1<br>0.01<br>0.001 | 100<br>100<br>70 |
| 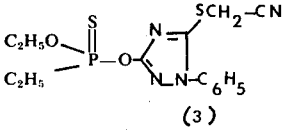 (3) | 0.1<br>0.01<br>0.001 | 100<br>100<br>100 |
| 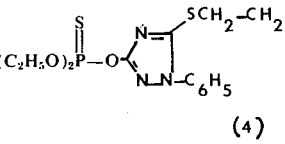 (4) | 0.1<br>0.01<br>0.001 | 100<br>100<br>100 |

TABLE 3

(Myzus test)

| Active compound | Active compound concentration in % | Degree of destruction in % after 1 day |
|---|---|---|
| (CH$_3$O)$_2$P(=S)—O—[3-methylpyrazol-5-yl] (A) (known) | 0.1 | 0 |
| (C$_2$H$_5$O)$_2$P(=S)—O—[3-methylpyrazol-5-yl] (B) (known) | 0.1<br>0.01 | 99<br>40 |
| (C$_2$H$_5$O)$_2$P(=S)—O—[4-(SCH$_2$—CN), 1-C$_6$H$_5$-imidazol-2-yl] (1) | 0.1<br>0.01 | 100<br>90 |
| (C$_2$H$_5$O)(C$_2$H$_5$)P(=S)—O—[4-(SCH$_2$—CN), 1-C$_6$H$_5$-imidazol-2-yl] (3) | 0.1<br>0.01 | 100<br>100 |
| (C$_2$H$_5$O)$_2$P(=S)—O—[4-(SCH$_2$—CH$_2$—CN), 1-C$_6$H$_5$-imidazol-2-yl] (4) | 0.1<br>0.01 | 100<br>99 |

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed, whereas 0% means that none of the spider mites were killed.

The active compounds, the concentrations of the active compounds, the evaluation times and the results can be seen from the following table:

TABLE 4

| Active compound | (Tetranychus test) Active compound concentration in % | Degree of destruction in % after 2 days |
|---|---|---|
| 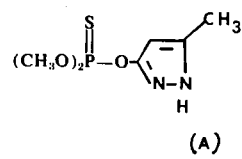 (A) (known) | 0.1 | 0 |
| 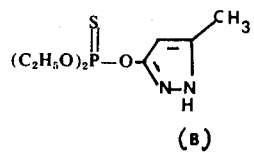 (B) (known) | 0.1<br>0.01 | 50<br>0 |
| 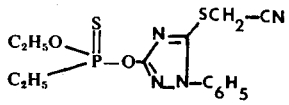 | 0.1<br>0.01 | 100<br>55 |

EXAMPLE 5

Test with parasitic fly larvae (*Lucilia cuprina res.*)

Solvent: 35 parts by weight of ethylene polyglycol monomethyl ether

Emulsifier: 35 parts by weight of nonylphenol polyglycol ether

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina res.*) were introduced into a test tube which contained approximately 2 ml of horse muscle. 0.5 ml of the preparation of active compound was applied to this horse meat. After 24 hours, the degree of destruction in % was determined. 100% means that all larvae were killed and 0% means that no larvae were killed.

The test results obtained can be seen from the table which follows:

TABLE 5

| Active compound | (test with parasitic fly larvae/*Lucilia cuprina* res.) Active compound concentration in ppm | Degree of destruction in % |
|---|---|---|
| 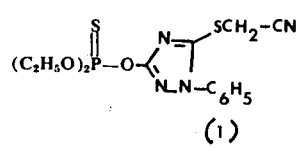 (1) | 100<br>30<br>10<br>3<br>1 | 100<br>100<br>100<br>>50<br>0 |

The process of this invention is illustrated in and by the following preparative Examples.

EXAMPLE 6

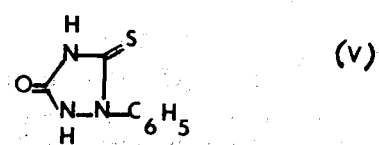

109 g of chlorocarbonic acid ethyl ester were added to a suspension of 96 g (1 mole) of dried potassium thiocyanate in 500 ml of acetone, while keeping the exothermic reaction at a temperature of between 30° and 40°C by external cooling of the mixture or by an appropriately slow addition of the ester. The reaction solution was then stirred for appoximately 4 hours at 25° to 30°C and was subsequently added to a solution of 100 g of phenylhydrazine in 200 ml of acetone, which solution had beforehand been stirred for 3 hours. The reaction was slightly exothermic. The batch was stirred overnight, the precipitate which had separated out was filtered off, the solvent was evaporated off, a mixture of 800 ml of water and 100 ml of concentrated hydrochloric acid was added to the distillation residue, the batch was boiled for 2 hours and cooled, and the product was filtered off. The product thus obtained could be used directly for further operations without having to undergo additional purification processes. 100 to 110 g (52 to 55% of theory) of a crude product of melting point 218–225°C were obtained. A sample of 1-phenyl-3-oxo-5-thio-triazolidine-(1,2,4) recrystallized from acetonitrile melted at 235°C.

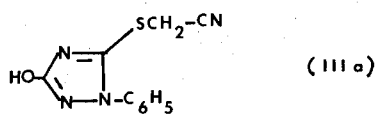

(IIIa)

0.2 mole of sodium methylate, followed by 16 g of chloroacetonitrile, was added to 39 g of (0.2 mole) of the product obtained as described under (a), in 200 ml of methanol. The reaction mixture was stirred for 4 hours at 50° to 60°C, cooled and poured into water; the residue was filtered off, dried and recrystallized from acetonitrile. This gave 36 g (78% of theory) of 1-phenyl-3-hydroxy-5-cyanomethylmercaptotriazole-(1,2,4) of melting point 178°C. (c) The compound of the formula

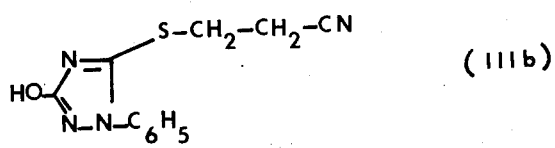

(IIIb)

could be prepared analogously in 53% yield; the product had a melting point of 183°C.

EXAMPLE 1

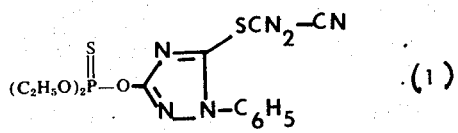

(1)

19 g (0.1 mole) of 0,0-diethylthionophosphoric acid diester chloride (IIIa) were added to a mixture of 23 g (0.1 mole) of 1-phenyl-3-hydroxy-5-cyanomethylmercaptotriazole-(1,2,4) in 300 ml of acetonitrile and 15 g of potassium carbonate. After stirring for 4 hours at 80°C, the reaction mixture was poured into water and taken up in benzene. The organic phase was washed and dried. The solvent was then distilled off under reduced pressure. The residue was subjected to "slight distillation". This gave 29 g (76% of theory) of 0,0-diethyl-0-[1-phenyl-5-cyanomethylmercapto-1,2,4-triazol(3)yl]-thionophosphoric acid ester having a refractive index $n_D^{20}$ of 1.5589. (e) The following compounds of the general formula

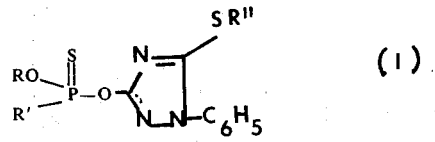

(1)

were prepared by analogous methods:

| Compound No. | R | R' | R'' | Physical properties (refractive index or melting point) |
|---|---|---|---|---|
| 2 | CH₃ | CH₃O | NC—CH₂ | melting point 82°C |
| 3 | C₂H₅ | C₂H₅ | NC—CH₂ | $N_D^{22}$: 1.5840 |
| 4 | C₂H₅ | C₂H₅O | NC—CH₂—CH₂ | $n_D^{22}$: 1.5640 |

It will be appreciated that the instant specification and examples are set forth by way of illustration and not limitation, and that various modifications and changes may be made without departing from the spirit and scope of the present invention.

What is claimed is:

1. An 0-alkyl-0-triazolyl-thionophosphoric-(phosphonic) acid ester of the formula in which
R is alkyl with 1 to 6 carbon atoms,
R' is alkyl or alkoxy with in either case 1 to 6 carbon atoms, and
R'' is cyanoalkyl with 1 to 4 carbon atoms.

2. A compound according to claim 1, in which R is straight-chain or branched alkyl with 1 to 5 carbon atoms, R' is straight-chain or branched alkyl or alkoxy with in either case 1 to 5 carbon atoms, and R'' is cyanoalkyl with 1 to 3 carbon atoms.

3. The compound according to claim 1 wherein such compound is 0,0-diethyl-0-[1-phenyl-5-cyanomethylmercapto-1,2,4-triazol(3)yl]-thionophosphoric acid ester of the formula

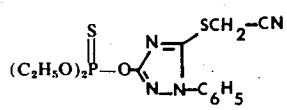

4. The compound according to claim 1 wherein such compound is 0,0-dimethyl-0-[1-phenyl-5-cyanomethylmercapto-1,2,4-triazol(3)yl]-thionophosphoric acid ester of the formula

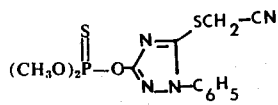

5. The compound according to claim 1 wherein such compound is 0-ethyl-0-[1-phenyl-5-cyanomethylmercapto-1,2,4-triazol(3)yl]-ethanethionophosphonic acid ester of the formula

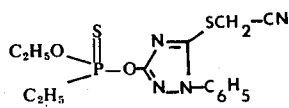

6. The compound according to claim 1 wherein such compound is 0,0-diethyl-0-[1-phenyl-5-(2-cyanoethylmercapto)-1,2,4-triazol(3)yl]-thionophosphoric acid ester of the formula

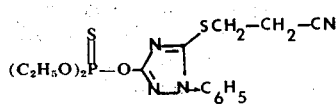

7. An insecticidal, acaricidal or nematicidal composition containing as active ingredient an insecticidally, acaricidally or nematicidally effective amount of a compound according to claim 1 in admixture with a diluent.

8. A method of combating insects, acarids or nematodes which comprises applying to the insects, acarids or nematodes or to a habitat thereof an insecticidally, acaricidally or nematicidally effective amount of a compound according to claim 1.

9. The method according to claim 8 in which said compound is
0,0-diethyl-0-[1-phenyl-5-cyanomethylmercapto-1,2,4-triazol(3)yl]-thionophosphoric acid ester,
0,0-dimethyl-0-[1-phenyl-5-cyanomethylmercapto-1,2,4-triazol(3)yl]-thionophosphoric acid ester,
0-ethyl-0-[1-phenyl-5-cyanomethylmercapto-1,2,4-triazol(3)yl]-ethanethionophosphonic acid ester, or
0,0-diethyl-0-[1-phenyl-5-(2-cyanoethylmercapto)-1,2,4-triazol(3)yl]-thionophosphoric acid ester.

* * * * *